(12) United States Patent
McDaniel

(10) Patent No.: US 6,544,232 B1
(45) Date of Patent: Apr. 8, 2003

(54) CYSTOSTOMY CATHETER BELT

(76) Inventor: Gladys P. McDaniel, 320 Merriman Rd., Louisville, KY (US) 40207

(*) Notice: Subject to any disclaimer, the term of this patent is extended or adjusted under 35 U.S.C. 154(b) by 77 days.

(21) Appl. No.: 09/618,655

(22) Filed: Jul. 18, 2000

(51) Int. Cl.[7] .................................................. A61M 5/32
(52) U.S. Cl. ...................... 604/174; 604/179; 604/181; 128/DIG. 26
(58) Field of Search ................................. 604/179, 327, 604/174, 181, 182, 183, 184, 185, 180; 128/673, DIG. 24, DIG. 25, DIG. 26

(56) References Cited

U.S. PATENT DOCUMENTS

| | | |
|---|---|---|
| 4,662,873 A | 5/1987 | Lash et al. |
| 4,738,661 A | 4/1988 | Marut |
| 4,763,648 A * | 8/1988 | Wyatt .......................... 128/673 |
| 5,087,251 A * | 2/1992 | Heyman et al. ............ 604/327 |
| 5,188,608 A | 2/1993 | Fritts |
| 5,304,145 A | 4/1994 | Blair |
| 5,403,285 A | 4/1995 | Roberts |
| 5,425,719 A | 6/1995 | Lessing, Jr. |
| 5,468,229 A | 11/1995 | Chandler |
| 5,496,282 A | 3/1996 | Militzer et al. |
| 5,643,236 A * | 7/1997 | Hadley ........................ 604/353 |
| 5,688,248 A | 11/1997 | Lessing, Jr. |
| 5,897,519 A | 4/1999 | Shesol et al. |
| 6,296,164 B1 * | 10/2001 | Russo ......................... 224/602 |

* cited by examiner

Primary Examiner—Thomas Denion
Assistant Examiner—Binh Tran
(74) Attorney, Agent, or Firm—Carrithers Law Office; David W. Carrithers

(57) ABSTRACT

A belt and catheter attachment apparatus for stabilizing, cushioning, protecting, and covering an implanted peritoneal catheter for applications with cytostome treatments where the catheter exits from the abdomen of a user and is worn by the user in bed and as well as remote locations. The belt includes a body of fabric designed to encircle the patient with means for holding such as fasteners with hook and loop features for securing the distal ends together. The front portion of the belt includes a plurality of spaced apart wide loops or bands, preferably three loops or bands, sewn on to the front of the belt to hold the attachment apparatus defining a manifold, a distal end of the catheter tube, the two-way valve, the catheter sample port, and receptacle drain tube attachment fitting with in a pouch formed by a flap having extending from the upper edge of the front portion of the belt, and folds downwardly covering the front portion of the belt covering the retaining loops, the distal end of the catheter, the two-way valve, a sample port, and the catheter bay attachment fitting.

2 Claims, 5 Drawing Sheets

CYSTOSTOMY CATHETER BELT

BACKGROUND OF THE INVENTION

1. Field of the Invention

The present invention relates generally to a belt for holding a cystostomy catheter device stable against a user, thereby virtually preventing any trauma to an exit site from which the catheter device extends out of the user's body and is intended for use in cytostome applications where the patient is recovering from kidney of bladder related surgery and the fluid is collected via a catheter inserted into the urethra in the pubic area and temporarily held into place by stitches, staples or the like. The present invention eliminates or is an alternative means of holding the tubing into place without the use of an adhesive used as a conventional means to hold the tubes into place. Replacing the adhesive eliminates serious problems some patients have due to an allergic reaction to the adhesive or latex materials. In addition to supporting the catheter tubes, the belt cushions, covers, and protects the apparatus connecting to the catheter and includes a manifold assembly with quick connections, a two-way valve and sample ports.

2. Description of the Related Art

In cystostomy, the peritoneal catheter is inserted through the abdomen in the pubic area to drain fluid from the bladder. The catheter is a soft plastic tube surgically placed in the patient's lower abdomen. Although the present invention may also be utilized to support a dialysis catheter, the instant invention incorporates design features providing advantages which are not necessary for dialysis catheter holding devices.

Dialysis is a way of cleaning the blood when a person's kidneys can no longer perform their function. Dialysis substitutes for the kidneys by removing the body's wastes, which include excess salt and water. A peritoneal catheter is placed in the patient's abdomen and used in dialysis for filtering the blood across a lining of the patient's abdominal cavity as set forth and described in U.S. Pat. No. 5,496,282, and hereby incorporated by reference. The lining is called the peritoneum and serves as a natural filtering membrane. In peritoneal dialysis, wastes are removed by means of a sterile cleansing fluid which is washed in and out of the abdomen in cycles. The cleansing fluid enters the abdomen through the catheter. Wastes from the blood pass through the peritoneal membrane into the cleansing fluid. Later, when the filtering process is completed, the fluid leaves the body through the catheter. Another name for peritoneal dialysis is "Continuous Ambulatory Peritoneal Dialysis" (CAPD). The process of CAPD does not require the patient to use a dialysis machine, and may be performed at home, at the work place or anywhere where a calm and semi-sterile environment can be temporarily established. Because dialysis is usually, if not always accomplished while the patient is immobile, the belt or other means of holding a dialysis catheter is designed to hold the catheter immobile in the region where the catheter is inserted into the abdominal cavity. Support for holding the auxiliary tubing and providing the patient with a means of easily moving about is typically not a high priority, nor should it be.

However, the instant invention provides a peritoneal dialysis device for supporting a cystostomy catheter used for bladder dysfunction cases wherein a tube extends from the bladder through the peritoneal cavity wall. Patients on peritoneal cystostomy are constantly inconvenienced by the long plastic tube, generally about two feet in length, exiting from their lower abdomen. The exit site in the abdomen is easily irritated by the tube being tugged and moved as the person moves. Usually the cystostomy catheter is temporary and the patient is encouraged to move about during the day sometimes for weeks or months until the recovery period is complete and the bladder functions normally. Of course, in some cases the catheter is worn indefinitely. Injuries due to movement of the catheter where it enters the abdomen or is secured by stitches, staples, or the like, occur daily and cause problems ranging from simple pain and discomfort to severe infections and peritonitis.

The problem area is in supporting the catheter tubing. Tape is a good temporary solution but, over time, tends to really irritate the skin. Some patients have even required medical treatment because skin breakdown was so severe. Securing the catheter apparatus by merely taping a section of the catheter apparatus directly to the patient's body is unsatisfactory because frequent removal of the tape, as in the continuous ambulatory peritoneal dialysis treatment method, 4–6 times daily, can result in physical discomfort; the tape is not re-usable; the tape secures only a portion of the catheter apparatus, leaving the majority of the apparatus exposed; some people are allergic to the tape adhesive; and the taping method is aesthetically undesirable because it inhibits the pursuit of a normal, active lifestyle, including physical intimacy.

SUMMARY OF THE INVENTION

The present invention provides a catheter support belt for stabilizing an implanted peritoneal cystostomy catheter exiting from the abdomen of a user and having a two-way valve at one end. The belt includes a band of fabric designed to encircle the patient, at least two fasteners incorporating means of attachment such as with hook and loop features, and a receptacle. The front portion of the belt includes a plurality of spaced apart wide loops or bands, preferably three, sewn on to the front of the belt to hold the distal end of the catheter, the valve, and a catheter bag attachment fitting. A first vertical flap having a slit forming a hole therein extends from the upper edge of the front portion of the belt, and folds downwardly covering the front portion of the belt, the loops and the distal end of the catheter, the valve, a sample port, and the catheter bay attachment fitting. A pair of second short side flaps extend outwardly from the edges of the first vertical flap. Means for attachment such as one of more hooks sewn into or connected to the underside of the short flaps cooperatively engage mating hook loops sewn or otherwise fastened to the outer surface of the front of the belt. Cooperatively engaging the short flap hooks with the belt hook loops holds the flap in position over the apparatus forming a protective support pouch and providing a smooth surface and appearance. Means for holding such as hooks extend from the distal end of the belt for cooperatively engaging a plurality of hook loops fastened to the exterior surface of the belt for adjustably holding the ends of the belt together. The support pouch is used to securely hold the valve end of the catheter, bag line attachment fitting, valve, and sample port against the belt body. The receptacle generally consists of a plastic bag or pouch which may be hung from a support member such as the bed frame or could be carried by the user and supported by a conventional belt, shoulder strap, handle, or supported by other structures in close proximity to the user.

The principle object of the present invention is to provide a more convenient, comfortable and desirable device for use securing surgically-implanted peritoneal catheters for cystostomy in a durable, re-usable adjustable belt pack and provide a means for taking samples from the manifold assembly held therein by simply opening of closing valves and providing a sample port. Moreover, the belt enables the wearer to move and actively pursue a normal life style while wearing the belt.

The invention solves such problems by having a plurality of button holes in the belt throughout its length which cooperate with a button fastening system on the pouch to permit a wide range of adjustment of the belt.

Other objects, advantages and capabilities of the invention will become apparent from the following description taken in conjunction with the accompanying drawings showing preferred embodiments of the invention.

BRIEF DESCRIPTION OF THE DRAWINGS

A better understanding of the present invention will be had upon reference to the following description in conjunction with the accompanying drawings in which like numerals refer to like parts throughout the several views and wherein.

DETAILED DESCRIPTION OF THE PREFERRED EMBODIMENT

Figure 1:
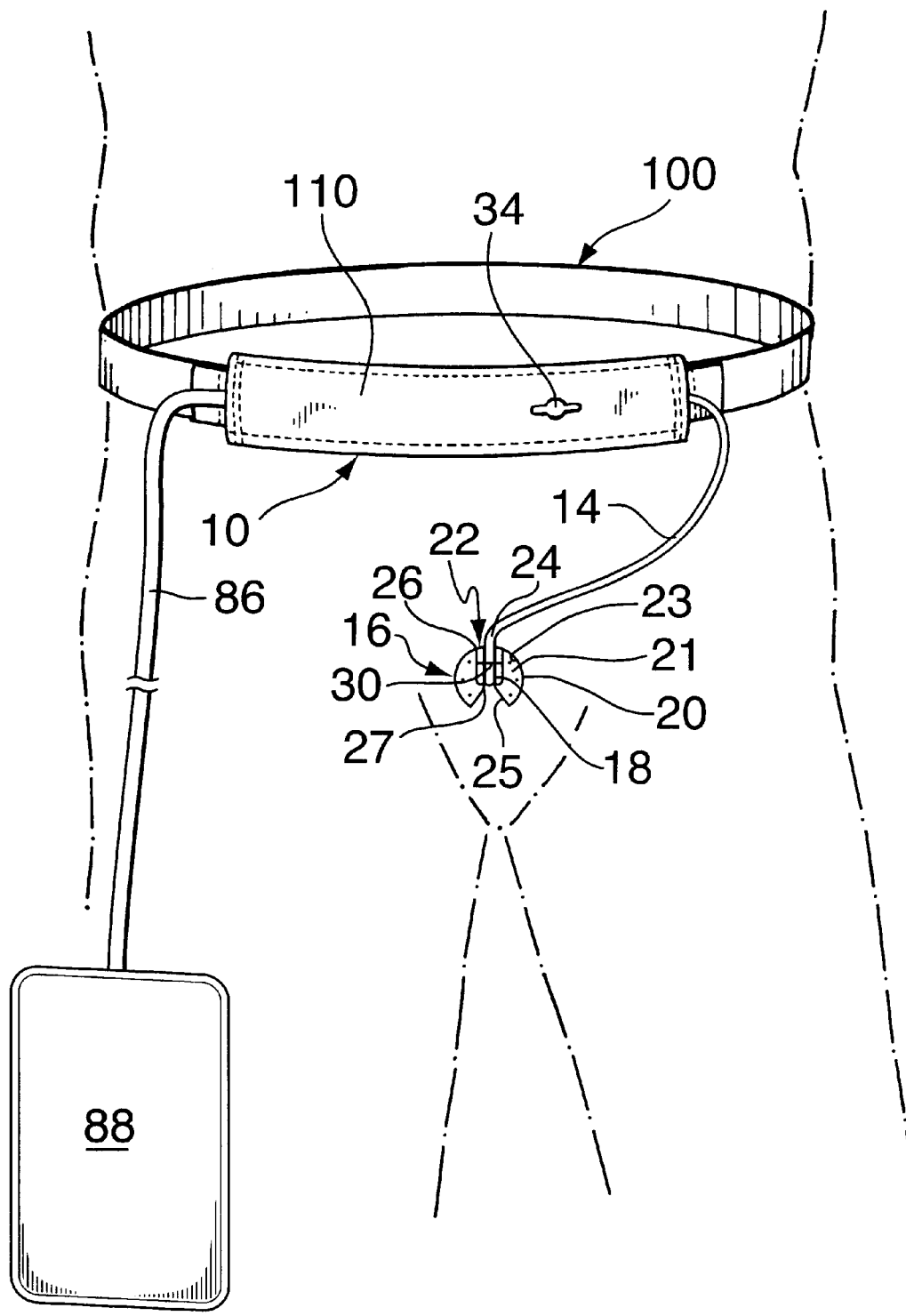
FIG. 1 is a perspective view of the peritoneal cystostomy-dialysis catheter belt of the present invention shown on the patient connected to a collection bag and showing the front protective flap covering the manifold assembly.
Figure 2:
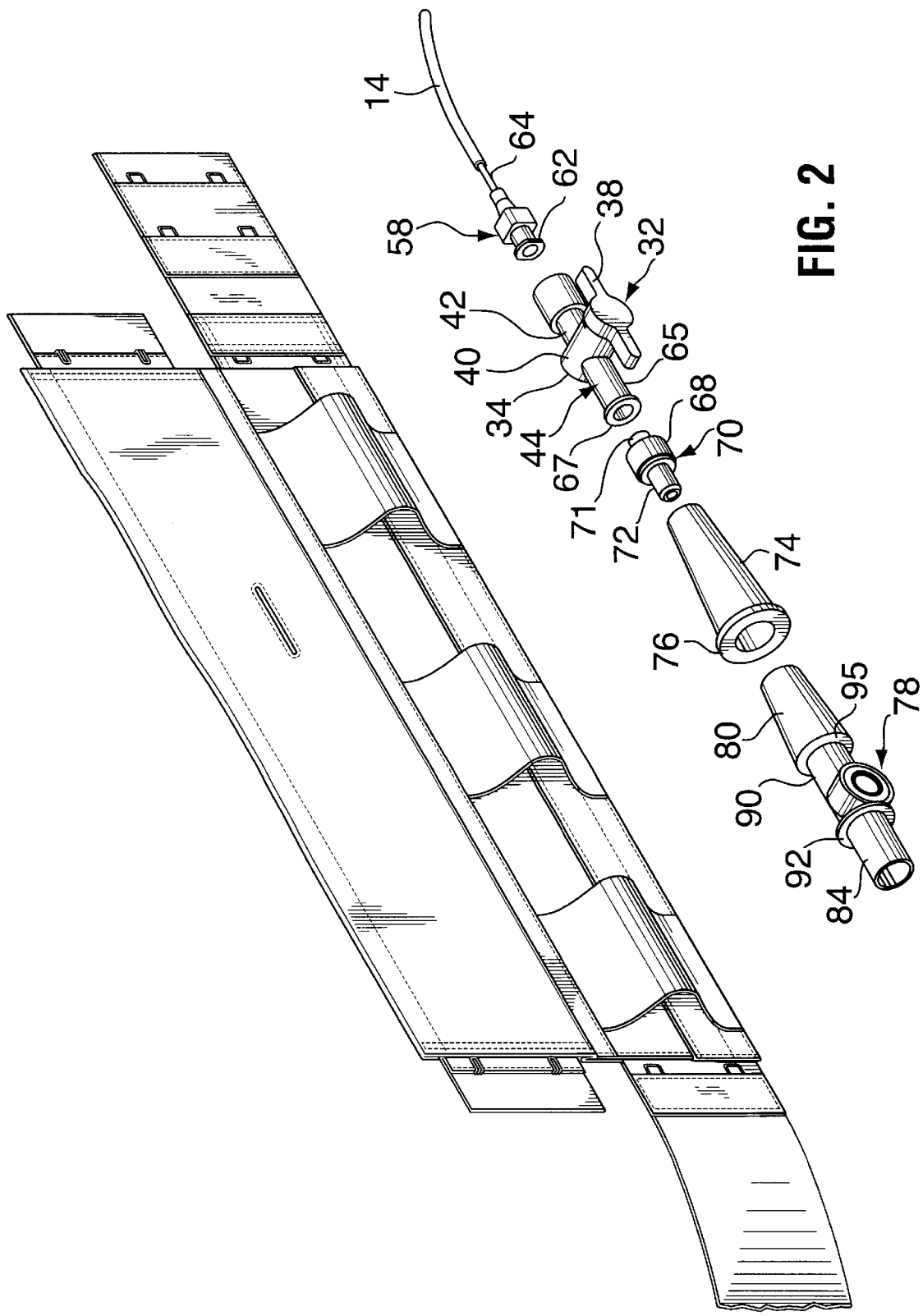
FIG. 2 is a perspective exploded view showing the manifold assembly positioned in alignment with the loops for cooperatively engaging the manifold assembly and securing limited movement within the loops of the front panel.
Figure 3:
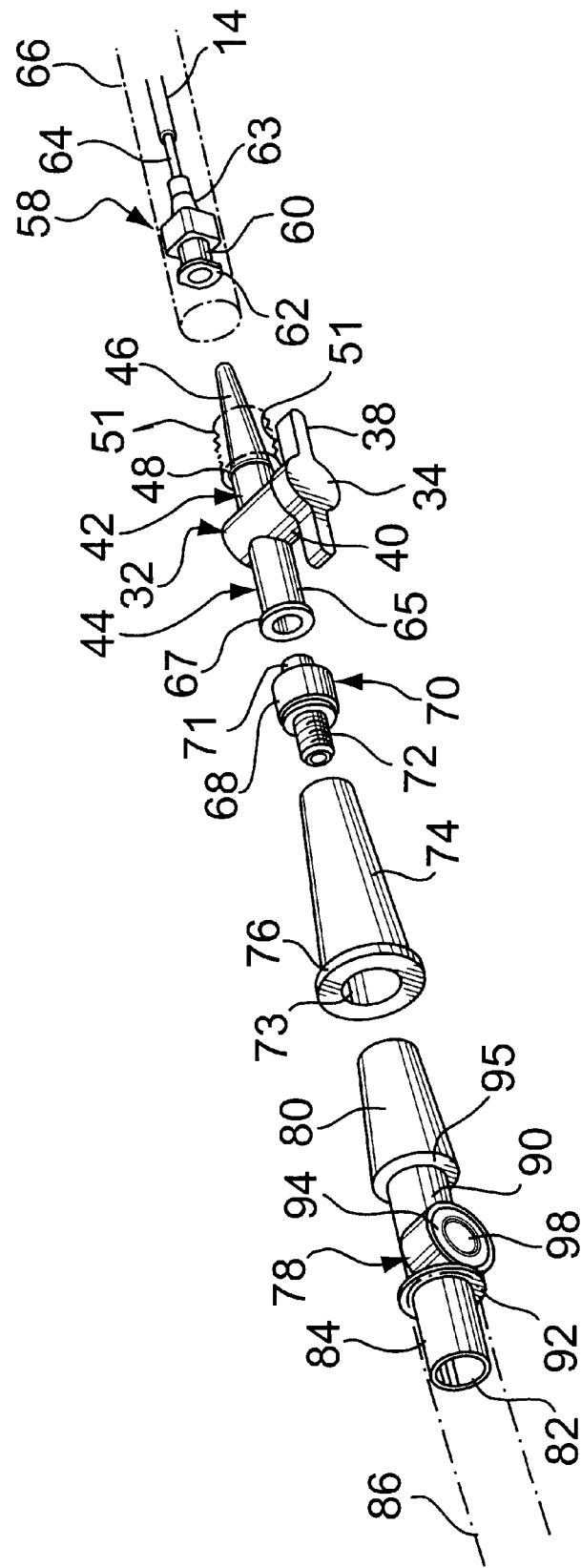
FIG. 3 is a perspective exploded view showing the valve assembly of FIG. 2 in more detail.
Figure 4:
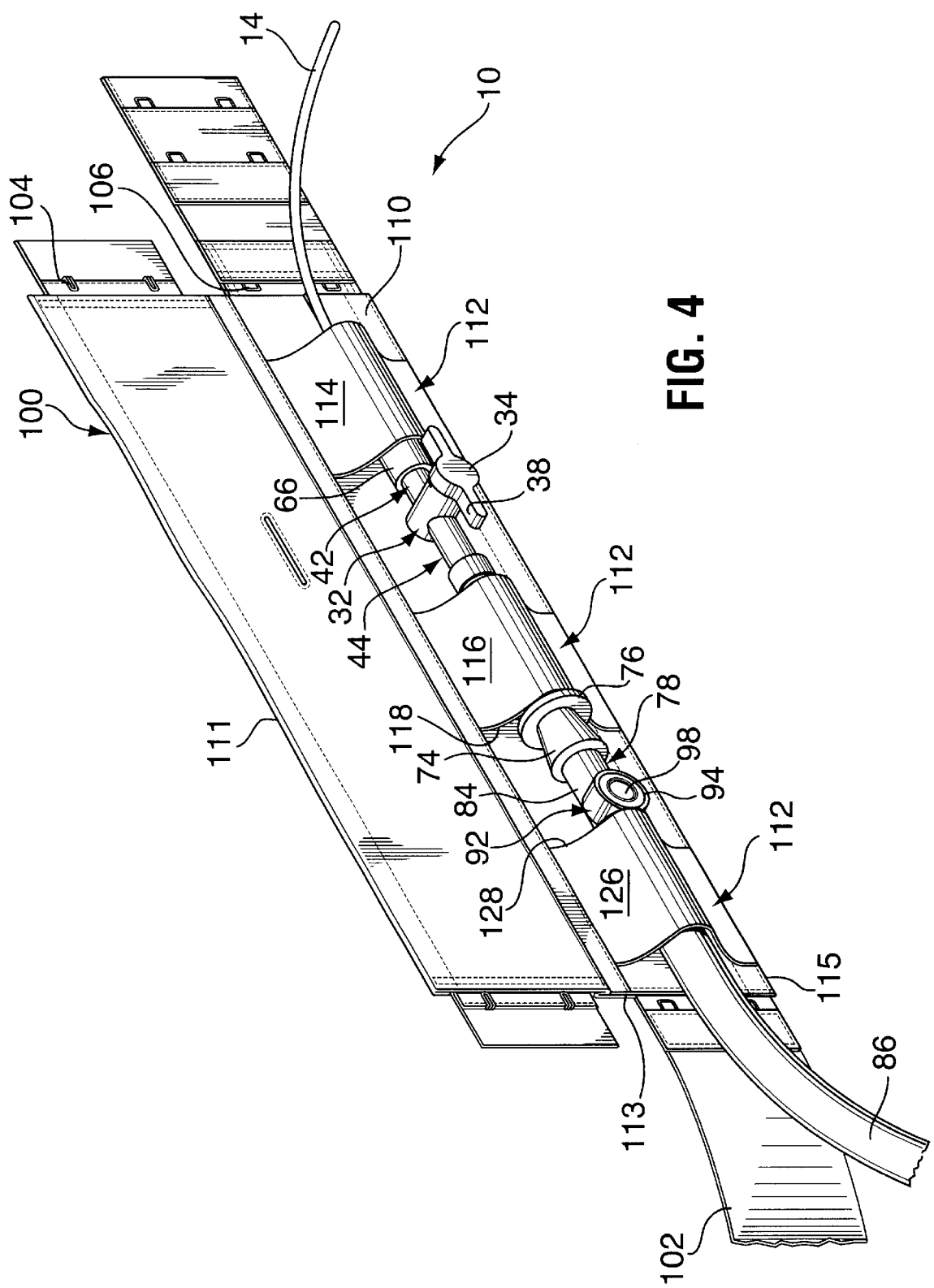
FIG. 4 is a perspective side view of FIG. 2, showing the manifold assembly securely held within the loops of the catheter belt and showing the catheter tube connection in the manifold exposed by lifting of the side flap of the front panel cover.
Figure 5:
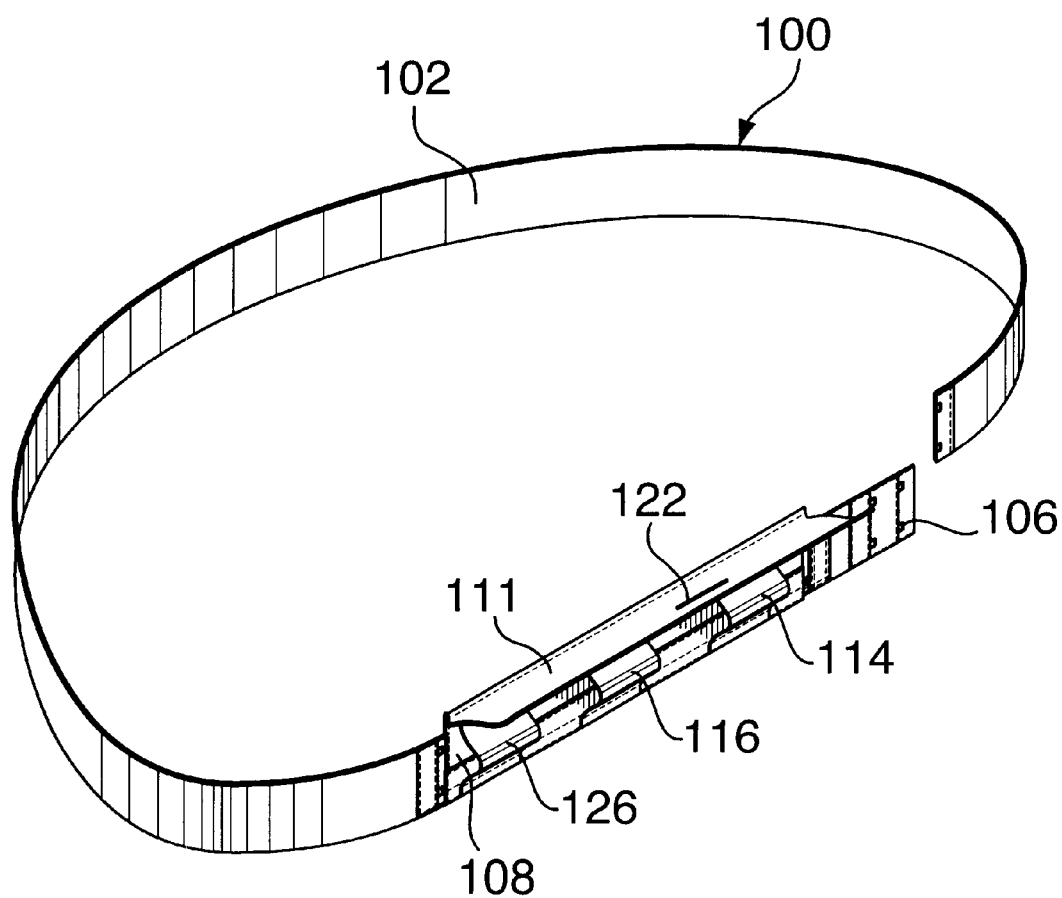
FIG. 5 is a front perspective view of the present invention showing the adjustable connecting loops and fasteners on the distal end of the belt.

With reference to the drawings, FIGS. 1–5 illustrate the peritoneal cystostomy catheter belt 10 of the present invention utilized with a selected caterer assembly in a cystostomy application.

Implanted within the abdomen is the catheter, not shown, in fluid connection with the bladder of a patient and connecting to a catheter tube 14 of a small diameter connecting to the distal end of the catheter. The tube exits the incision of the abdomen and protrudes outwardly through a center opening 18 of the tube holder 16. The tube holder 16 is further defined a base 20 forming a flat disc having a plurality of holes 21 around the periphery thereof for cooperatively engaging thread 23 or staples for securing the base 20 to the abdomen skin of the patient. The bottom portion of the base 20 includes a triangular shaped notch 25 extending from the center opening 18 whereby the inner edges of the notch form corners 27 that are almost contiguous at the opening 18 so that the catheter tube 14 can be forced in between the corners 27 into the opening and movably secured therein. Upon exiting the abdomen and extending through the opening 18 of the base 20, the catheter tube 14 curves ninety degrees and extends over a bridge 22 formed by a pair of side ribs 26 having a channel 24 formed thereinbetween. A means for holding such as a band or tie 30 holds the tube in the channel 24 directing the catheter tube 14 from the pubic area toward the belt extending around the waist of the patient.

The catheter tubing 14 is connected to a valve assembly 32. The valve 32 is a type of ball or plunger valve having a generally cylindrical shaped plunger having an opening therethrough and a stem 34 extending from a top of the plunger having a opposing handle projections 38 extending therefrom for rotation by the patients fingers. The plunger is seated in a complementary sized and shaped housing 40 having a tubular intake neck 42 and tubular exit neck opening 44. The distal end of the entry neck 42 includes a tapered portion 46 and includes a collar 48 at the junction of the tapered portion and the cylindrical portion of the neck 42. A connecting sleeve 50 mounted to the entry neck 42, includes internal threads 51 extending from the inner surface thereof. The connecting sleeve 50 has an open distal end 52 and a partially open proximate end 54.

A first connector 58 having a cylindrical body 60 includes a flange 62 extending from a distal end therearound for cooperatively and threadably engaging the internal threads 51 of the sleeve 50 of the valve neck 42 forming fluid communication therewith. The opposing distal end of the connector defines a conical portion 63 having a slender metal tube 64 protruding therefrom for cooperative engagement with the distal end of the catheter tube 14.

The tapered portion 46 of the valve assembly 32 is inserted into the cylindrical body 60 and the flange 62 cooperatively engages the internal threads 51 of the sleeve 50 forming a liquid tight seal therebetween. A protective tube 66 of the same external diameter as the sleeve 50 abuts the sleeve 50 and extends coaxially around the connector 58 including the metal tube and a portion of the catheter tube connecting thereto.

The opposing distal end of the valve 32 defines a short cylindrical tube section 65 having a peripheral flange 67 extending around the end thereof. The flange 67 cooperatively and threadably engages the internal threads of a sleeve 68 of a second connector 70 having a short center tubular member 71 extending therefrom into the tube section 65 of the valve neck 44. The external opposing end of the second connector 70 defines a threaded tubular member 72 of smaller diameter than the sleeve 70 and the tubular member 72 threadably engages a hollow conical shaped connector or cone 74 composed of an elastomer or other rubber or plastic material which includes a flange 76 extending around the periphery of the larger diameter end 73 of the cone 74.

A sampler 78 defining a hollow plastic tube includes a first tapered end 80 which cooperatively extends into and cooperatively engages the large diameter end 73 of the cone 74 and is secured by a frictional fit with the elastomer. The sample port 94 includes an opposing distal end 82 defining a tubular cylindrical member 84 or uniform diameter which cooperatively engages a plastic tube 86 which drains into a collection bag 88. The sampler 78 also includes a center section 90 including an external flange 92 extending around the periphery thereof between the center section 90 and the tubular cylindrical member 84. The center section 90 further defines a tubular member of uniform diameter connecting the tubular cylindrical member 84 with the first tapered end 80. The first tapered end 80 is of a larger external diameter than the center section 90 thereby forming a step or flange 95 extending therearound.

More particularly, the sample 78 includes a sample port 94 defining a short cylindrical body 96 having an aperture therein and the body extends outwardly from and normal to the center section 90. The sample port 94 includes a membrane or other semipermeable elastomeric member 98 wherein a needle can be inserted through the membrane for withdrawing fluid therefrom and upon withdrawal of the needle the member 98 is self sealing.

A belt 100 developed for use with the above described catheter assembly or similar apparatus is fabricated and designed for stabilizing an implanted cystostomy catheter exiting from the abdomen of a user. The belt 100 includes a band 102 of fabric designed to encircle the patient, at least two fasteners incorporating means of attachment such as with hook 104 and loop 106 features.

It should be noted that ideally the belt 100 must be positioned in close proximity to the bladder of the user and is worn low on the pelvic area for use with cystostomy applications which present a problem when utilizing the belt when the patient wishes to be mobile. Although catheter type belts are known in the art and worn by dialysis patients wherein the belt is worn high around the waist in closer proximity to the kidneys, the nature of support of the catheter assembly for cystostomy patients is different. The dialysis catheter belts are designed for supporting short tubes exiting the kidneys or the abdominal cavity of the patient. Cystostomy applications require that the patients drain fluid from the bladder or section of the urethra in close proximity thereto, therefor a long length of tubing is necessary to use a belt which fits around the waist of the patient comfortably and supports the catheter assembly and tubes from the bladder and collection bag. The belt must utilize support structure which maintains flexibility to allow the user to be mobile, even leaving the room dressed in street clothing and allowing the catheter bag 88 to be temporarily disconnected and still hold the tubing from the bladder securely in position.

More particularly, the front portion 108 of the belt 100 defines a generally flat panel 110 of material which may be reinforced by use of two of more layers of fabric attached together with thread, glue or the like forming a base. It is contemplated that an insert such as a strip of cardboard or plastic material can be inserted in-between a double layer of material to add structural strength and rigidity to the panel while maintaining the general flexibility of same to maintain comfort to the user. The belt panel 110 includes a cover flap 111 attached, preferably to the top edge 113, or alternatively to the bottom edge 115 for covering the catheter apparatus. The belt panel 110 includes a plurality of spaced apart wide loops or bands 112, preferably three, sewn on to the front of the belt panel 110 to hold the catheter assembly (connections, valves, and sample port in the desired position. The loops 112 are composed of a cloth of polymer material comprising a fabric, knit or weave, preferably an elastic material which will give yet retain shape and memory. The distal ends of the loops 112 are attached to the top edge 113 and bottom edge 115 of the front panel 110 by means of attachment such as sewing, adhesives, rivets, tape, staples, or the like. The length of the bands 112 are dependent upon the length of the components which comprise the catheter assembly and are spaced to secure the sections of the tubing at the joints. For instance, as shown in the drawings, the protective tube 66 extending over the slender metal tube 64 fits within and is generally covered by a first loop 114. A second loop 116 is spaced apart from and in alignment with the first loop 114 and covers the cone 74. Moreover, the cone flange 76 abuts the loop end edge 118 limiting horizontal movement thereof. The valve stem 34 extends through an opening defining a button or reinforced slit 122 positioned between the first loop 114 and the second loop 116 so that upon closing the cover flap 111, the valve stem 34 and valve handle members 38 extend through the reinforced slit 122 for easy access to the user. The reinforced slit 122 is sized and shaped to hold the valve 32 securely in horizontal and vertical alignment.

A third loop 126 is attached to the front panel 110 and is spaced apart from and in alignment with the first loop 114 and second loop 116. The third loop 126 is spaced apart from the second loop 116 a distance sufficient to provide access to the sample port 94 of the sampler 78. The tubular cylindrical member 84 of the sampler 78 is covered by the third loop 126 together with a portion of the collection bag tube 86 cooperatively engaging the tubular cylindrical member 84. The external flange 92 of the sample 78 abuts the interior vertical edge 128 of the third loop 126.

The loops 112 cooperatively engage the sections of the catheter assembly to firmly and securely hold the apparatus in position, allowing the assembly to flex, yet maintaining positive pressure to prevent lateral or vertical slippage of the catheter assembly. The belt 100 provides a means for turning the valve 32 on or off to connect or disconnect the discharge tubing and take and collect samples. The valve 32 of the instant invention is particular important. While connectors or couplings used with kidney dialysis belts are often referred to as valves, they are primarily used for connection purposes. While a check valve (not shown) may be used in the line to prevent backflow of liquid when connecting or disconnecting the collector bag, the valve 32 of the instant invention is used to control discharge of the fluid from the bladder. Because surgery often partially paralyzes the bladder, the user of the catheter apparatus is allowed to let fluids drain into a bag overnight, but is required to stop the flow for predetermined periods during the day in order to retrain the bladder into holding and retaining the fluid and exercising the elasticity of the bladder. Thus, frequent disconnection from the collection bag is necessary. A stopper may be disposed into the tubular cylindrical member 84 in order to disconnect the tube 86 therefrom as a additional safety precaution to prevent leaking. The mobility of the user when disconnected and the weight and dimensions of the cystostomy catheter apparatus, and tubing require specialized support apparatus to provide a flexible, resilient, belt 110 providing limited but supported movement for the user.

Means for attachment of the cover flap 111 to the front panel 110 such as one of more hooks sewn into or connected to the underside of the short flaps cooperatively engage mating hook loops sewn or otherwise fastened to the outer surface of the front of the belt 110. Cooperatively engaging the short flap hooks with the belt hook loops holds the flap in position over the apparatus forming a protective support pouch and providing a smooth surface and appearance. Means for holding such as hooks extend from the distal end of the belt for cooperatively engaging a plurality of hook loops fastened to the exterior surface of the belt for adjustably holding the ends of the belt together. The belt 100 is used to securely hold the valve end of the catheter, bag line attachment fitting, valve, and sample port against the belt body. Hook and eye attachment apparatus as well as hook and eye extenders utilizing hooks, eyes, and short strips of elastic material, may be used to connect the distal ends of the belt and allow lengthening of the belt 100 depending upon the physical size of the user.

The receptacle generally consists of a plastic bag or pouch which may be hung from a support member such as the bed frame or could be carried by the user and supported by a handle, or supported by other structures in close proximity to the user.

The foregoing detailed description is given primarily for clearness of understanding and no unnecessary limitations are to be understood therefrom, for modifications will become obvious to those skilled in the art based upon more recent disclosures and may be made without departing from the spirit of the invention and scope of the appended claims.

I claim:

1. A cystostomy catheter belt, comprising:

a belt comprising a band of fabric defining top and bottom edges and having a first distal end and a second distal end detachably connecting together by means of attachment, said belt including a front portion defining a flat panel base, a cover flap attaching to preferably to a selected said top edge or said bottom edge of said belt, said cover flap including a hole therein for disposing a valve stem therethrough, and a plurality of spaced apart wide loops attaching to said front panel for holding a catheter assembly in position;

said cover being continuous and extending over said plurality of spaced apart wide loops; and said catheter assembly comprising a catheter, a tube connecting said catheter to a valve, a sample port, a tube connecting said valve to a receptacle.

2. A cystostomy catheter belt comprising a belt comprising a band of fabric defining top and bottom edges and having a first distal end and a second distal end detachably connecting together by means of attachment, said belt including a front portion defining a flat panel base, a cover flap attaching to preferably to a selected said top edge or said bottom edge of said belt, said cover flap including a hole therein for disposing a valve stem therethrough, and a plurality of spaced apart wide loops attaching to said front panel for holding a catheter assembly in position, and said cover being continuous and extending over said plurality of spaced apart wide loops.

* * * * *